United States Patent [19]

Commandeur et al.

[11] Patent Number: 5,446,228
[45] Date of Patent: Aug. 29, 1995

[54] BENZYLTOLUENES/BENZYLXYLENES DIELECTRIC COMPOSITIONS

[75] Inventors: Raymond Commandeur, Vizille; Pierre Jay, Saint-Dizier Au Mont D'Or; Noëlle Berger, Ecully, all of France

[73] Assignee: Elf Atochem S.A., Puteaux, France

[21] Appl. No.: 980,736

[22] Filed: Nov. 24, 1992

[30] Foreign Application Priority Data

Nov. 26, 1991 [FR] France ................... 91 14585

[51] Int. Cl.⁶ .................... H01B 3/22; H01G 4/22
[52] U.S. Cl. ...................... 585/6.3; 585/11; 585/25
[58] Field of Search ................ 585/6.3, 11, 25

[56] References Cited

U.S. PATENT DOCUMENTS 5,017,733 5/1991 Sato et al. .................. 585/6.3

FOREIGN PATENT DOCUMENTS 0384818 8/1990 European Pat. Off. .
0444989 9/1991 European Pat. Off. .
0446086 9/1991 European Pat. Off. .

*Primary Examiner*—Asok Pal
*Attorney, Agent, or Firm*—Burns, Doane, Swecker & Mathis

[57] ABSTRACT

Benzyltoluene/benzylxylene admixtures, easily prepared via Friedel-Crafts condensation of benzyl chloride with a mixture of toluene and xylene, are useful dielectric oils exhibiting improved rigidity and are well suited for inclusion in voltage transformers, capacitors, electrical cables, and the like.

6 Claims, 1 Drawing Sheet

ATOCHEM

BENZYLTOLUENES/BENZYLXYLENES DIELECTRIC COMPOSITIONS

BACKGROUND OF THE INVENTION

1. Field of the Invention

The present invention relates to novel dielectric compositions based on particular admixtures of benzyltoluenes and benzylxylenes.

2. Description of the Prior Art

EP-136,230 describes compositions based on benzyltoluene oligomers which remain liquid at low temperatures without exhibiting a high viscosity.

EP-299,867 describes compositions based on (methylbenzyl)xylene and the higher homologs thereof.

And EP-466,086 describes dielectric mixtures of benzylxylene, benzyltoluene, (methylbenzyl)toluene and (methylbenzyl)xylene.

SUMMARY OF THE INVENTION

A major object of the present invention is the provision of unique compositions having better dielectric properties than the compositions described in EP-136,230 and EP-299,867, in particular in respect of the rigidity thereof which is measured by the breakdown voltage between two electrodes.

Briefly, the present invention features novel dielectric compositions comprising at least one oligomer of a benzyltoluene having the formula A1:

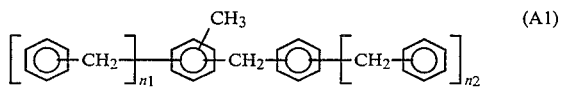

in which $n_1$ and $n_2 = 0$, 1 or 2, with the proviso that $n_1 + n_2$ is less than or equal to 3, and at least one oligomer of a benzylxylene having the formula A2:

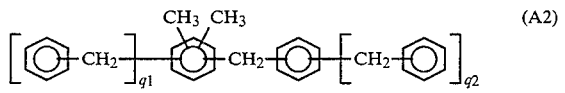

in which $q_1$ and $q_2 = 0$, 1 or 2, with the proviso that $q_1 + q_2$ is less than or equal to 3.

DETAILED DESCRIPTION OF THE PREFERRED EMBODIMENTS OF THE INVENTION

More particularly according to the present invention, benzyltoluene denotes the product of formula A1 in which $n_1$ and $n_2$ have the value 0. Benzylxylene denotes the product of formula A2 in which $q_1$ and $q_2$ have the value 0.

The compositions of the invention are useful electrical insulating oils well suited for inclusion in voltage transformers, capacitors or electrical cables, etc.

The compositions of the invention can also comprise the triphenylmethanes of formula B1:

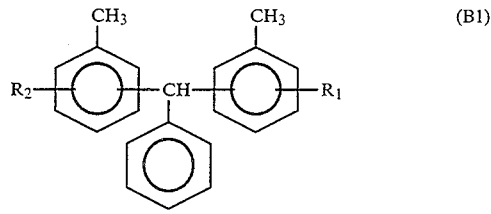

in which $R_1$ and $R_2$, which may be identical or different, are each hydrogen or a methyl radical.

Preferred compositions according to this invention comprise:

(a) 50 to 70 parts by weight of benzyltoluene,
(b) 15 to 25 parts by weight of benzylxylene,
(c) 10 to 20 parts by weight of any mixture of compounds A1 and A2 in which $n_1 + n_2 = 1$ and $q_1 + q_2 = 1$.

The above 10 to 20 parts by weight of triaryl compounds can also comprise triphenylmethanes of formula B1.

It has now been determined that such compositions of the invention do not crystallize at $-50°$ C.

The compositions according to the invention can be prepared by intimately admixing the products A1, A2 and optionally B1.

A1 can be prepared by condensation of benzyl chloride with toluene via a Friedel-Crafts (FC) reaction. A2 can be prepared by condensation of benzyl chloride with xylene, also via an FC reaction. B1 can be prepared by condensation of benzylidene chloride $C_6H_5$—$CHCl_2$ with toluene, xylene or a mixture of toluene and xylene.

In a preferred embodiment of the invention, benzyl chloride is condensed with a mixture of toluene and xylene; the mixture of A1 and A2 is thus directly prepared.

If the benzyl chloride contains benzylidene chloride, then triphenylmethanes of formula B1 are also formed.

Such FC condensation is per se known to this art. An inorganic halide or an inorganic acid can be used as a catalyst. Aluminum chloride, ferric chloride or sulfuric acid, for example, are representative such catalysts. FC condensations are described in EP-422,986 and EP-435,737, hereby expressly incorporated by reference.

In another preferred embodiment of the invention, a partial free-radical chlorination of the toluene is carried out in order to produce a mixture of benzyl chloride and toluene.

This mixture can optionally be rectified to remove the benzylidene chloride. The option thus exists of preparing (i) a mixture of toluene and benzyl chloride or (ii) a mixture of toluene, benzyl chloride and benzylidene chloride.

It is then sufficient to add xylene and to conduct an FC condensation, for example by addition of ferric chloride. Such free-radical chlorination is also per se known to this art. Similar chlorinations, followed by FC reaction, are described in EP-136,230, EP-299,867 and EP-466,086, also hereby expressly incorporated by reference.

After the FC condensation, the FC catalyst is removed by washing and then the excess xylene and toluene are removed by a simple distillation. The distillation can also be continued in order to recover the composition according to the invention, or a bottoms of heavy products can remain.

It may be that the compositions of the invention include a minor amount of organic chlorine emanating from impure starting materials bearing chlorine atoms on the benzene nuclei. It suffices to conduct a treatment with an alkaline agent. It is possible, for example, to thus employ the techniques described in EP-250,748 and EP-306,398, hereby expressly incorporated by reference. If ferric chloride is used as the FC catalyst, it is not necessary to remove it at the end of the FC condensation reaction. The excess toluene and xylene is removed by distillation, the distillation is continued in order to recover the compositions of the invention and the remaining distillation bottoms contain the iron chloride and any heavy products. This process is described in EP-422,986 and EP-435,737, also hereby expressly incorporated by reference.

According to the various dielectric applications, it is advantageous to purify the compositions of the invention using decolorizing earths or zeolites and then to add antioxidizing agents or acid acceptors thereto. Such conditioning treatments are known to this art and are described, for example, in EP-8,251 and EP-136,230.

It is also within the scope of this invention to incorporate other dielectric oils or inorganic oils typically used in electrical transformers to the products A1, A2 and optionally B1.

In order to further illustrate the present invention and the advantages thereof, the following specific examples are given, it being understood that same are intended only as illustrative and in nowise limitative.

EXAMPLE 1

There were introduced, into a 6 liter reactor equipped with a rotary stirrer and a vertical condenser whose outlet was connected to a water bubbler, using a dropping funnel, 10 mol of benzyl chloride at 99% purity in a mixture of:

(i) 34.8 mol of toluene
(ii) 5.2 mol of ortho-xylene containing 2 g of $FeCl_3$.

The addition was carried out over 3 hours at a temperature of 105° C. The reaction mixture was then maintained for 2 h at 100°–110° C. while purging with a stream of nitrogen (the theoretical amount of HCl was collected in the water bubbler).

The unreacted toluene and ortho-xylene were distilled on a rotary evaporator at a vacuum of 90 to 15 mm of Hg (11,880 to 1,980 Pa), the temperature of the bath of the evaporator ranging from 80° to 130° C.

The residue (1,649 g) was placed in a reactor equipped with a stirrer. It was heated to 150° C. at 16 mm Hg (2,112 Pa) of vacuum such as to remove the residual amount of toluene and ortho-xylene (15.4 g).

The residue was then treated with 36 g of sodium methoxide, with stirring and nitrogen purging, for 4 h, 30 min at a temperature of 293° C.

The mixture thus treated was placed in a round-bottomed distillation flask equipped with a 10 cm column fitted with large glass rings.

The distillation was carried out at a vacuum of 3 to 5 mm (396 to 660 Pa) of Hg. A 961 g fraction of compounds containing two aromatic rings was obtained with a passage temperature of the vapors of 100° to 148° C. The distillation was continued, which enabled 338 g of a fraction of compounds containing three aromatic rings, the vapors of which transferred at 207° to 235° C., to be obtained. The fractions of compounds containing two aromatic rings and containing three aromatic rings (of oligomer types A1 and A2) were mixed in a weight ratio of 84.8/15.2. This mixture had, based on chromatographic analysis, a benzyltoluene content of 65.2% and a benzylxylene content of 19.2%, the remainder being triaryls of formulae A1 and A2. The chlorine content was 2 ppm.

This product is designated BT/BX-A.

EXAMPLE 2

The procedure of Example 1 was repeated, but 10 mol of crude chloride were used in place of the 99% pure benzyl chloride. This crude benzyl chloride was obtained by partial photochlorination of toluene to provide the following mixture:

(i) 73.3% toluene,
(ii) 24.9% benzyl chloride,
(iii) 0.4% benzylidene chloride.

The toluene excess was separated by distillation. The distillation base constituted the crude benzyl chloride having the following composition:

(i) 0.03% toluene,
(ii) 93.64% benzyl chloride,
(iii) 3.1% benzylidene chloride, with the complement being benzyltoluene oligomers.

The condensation was carried out with a mixture of 34.8 mol of toluene and 5.2 mol of orthoxylene as in Example 1. After development and distillation, a mixture was obtained which had the following composition by weight:

(a) 65.2% benzyltoluene,
(b) 20.8% benzylxylene,
(c) 13.9% compounds containing three aromatic rings.

The chlorine content was 35 ppm.

The compounds containing three aromatic rings comprised a mixture of oligomers of A1 and A2 type with $n_1+n_2=1$ and $q_1+q_2=1$ and of oligomers B1.

This product is designated BT/BX-B.

EXAMPLE 3

The procedure of Example 2 was repeated, but replacing ortho-xylene with para-xylene.

The composition of the final mixture was the following:

(a) 67.2% benzyltoluene,
(b) 17.6% benzylxylene,
(c) 14.9% compounds containing three aromatic rings.

The compounds containing three aromatic rings were of the same type as those of Example 2.

The chlorine content was 142 ppm.

This product is designated BT/BX-C.

EXAMPLE 4

Dielectric tests:

Rigidity was measured and was compared with other dielectric oils.

BT06 was a mixture of oligomers of benzyltoluene according to EP-136,230, having the composition:

(i) 80 parts of benzyltoluene, the product A1 such that $n_1+n_2=0$,
(ii) 15 parts of product A1 such that $n_1+n_2=1$,
(iii) 5 parts of the mixture:
(a) product A1 with $n_1+n_2=2$
(b) product B1 in which $R_1$ and $R_2$ were hydrogen.

XX05 was a mixture of oligomers of (methylbenzyl)xylene according to EP-443,899, having the composition:

(i) 85 parts of:

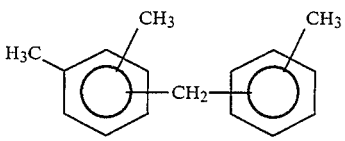

(ii) 12 parts of:

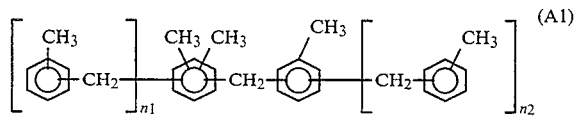

such that $n_1 + n_2 = 1$, (iii) 3 parts of:

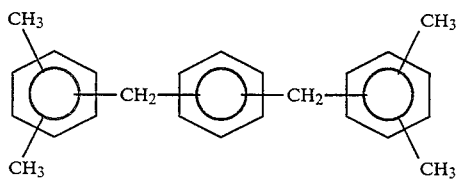

The breakdown voltage measurements were carried out under the following conditions:

(a) Electrodes: a gramophone needle ($\phi \approx 50$ μm) and a Rogowski disc,
(b) Gradient of 3,000 volts/second,
(c) Distance between electrodes = 5 mm,
(d) Room temperature.

BRIEF DESCRIPTION OF DRAWINGS

In the accompanying FIGURE of Drawing, the measurements are represented as Weibull diagrams which are commonly used to represent the statistical distribution of the dielectric rigidity of materials.

These diagrams evidences that the rigidity of the BT/BX mixtures was markedly superior to that of XX05, and slightly better than that of BT06. This was also observed from the means:

Figure 1A:
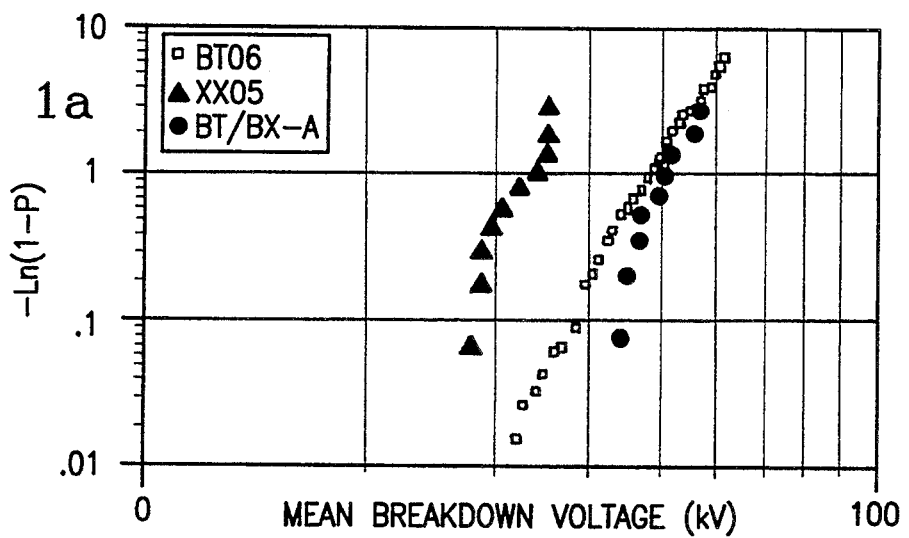
Figure 1B:
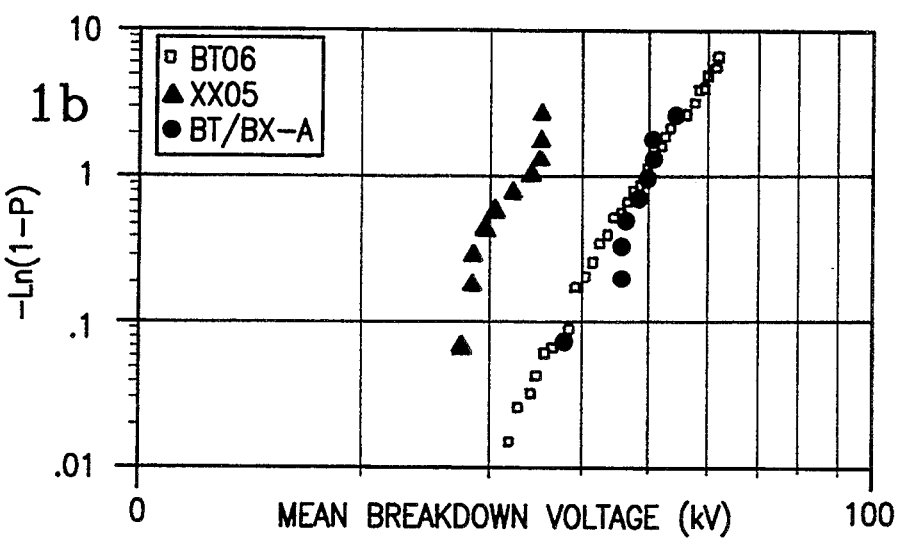
Figure 1C:
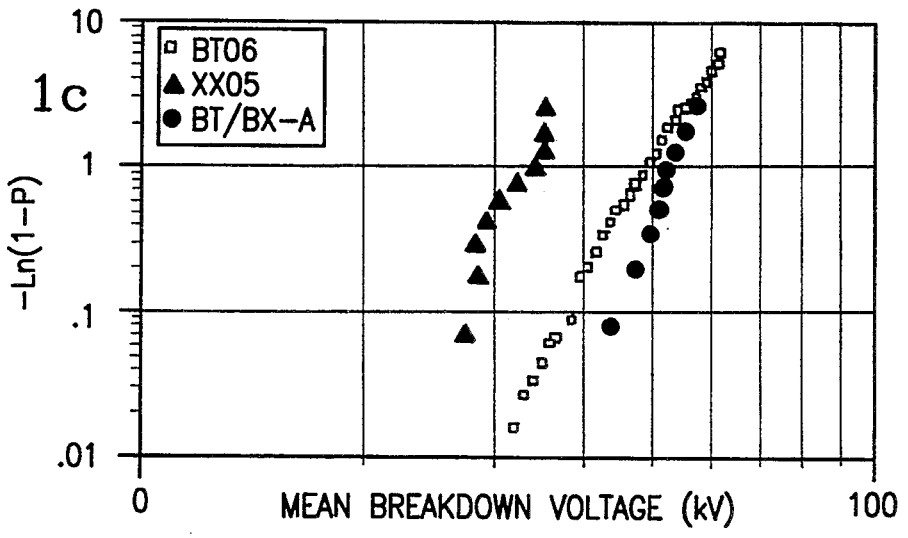

| Liquid | XX05 | BT06 | BT/BX-A | BT/BX-B | BT/BX-C |
|---|---|---|---|---|---|
| Mean breakdown voltage (kV) | 31.4 | 46.6 | 50.0 | 47.4 | 50.9 |

In said FIGURE of Drawing, -Ln(1-P) represents the Napierian logarithm of (1-P) and P is the cumulative probability.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dielectric composition consisting essentially of a mixture of benzylxylene and benzyltoluene.

2. The dielectric composition of claim 1 wherein said composition comprises 50 to 70 parts by weight of benzyltoluene and about 15 to 25 parts by weight of benzylxylene.

3. The dielectric composition of claim 1 which is uncrystallized at $-50°$ C.

4. A dielectric composition consisting essentially of a mixture of benzylxylene, benzyltoluene and at least one triphenylmethane having formula B1:

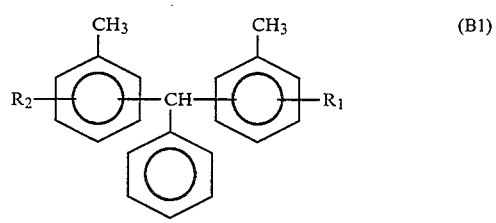

in which $R_1$ and $R_2$, which may be identical or different, are each hydrogen or a methyl radical.

5. In an electrical component that includes a dielectric liquid therefor, the improvement which comprises, as said dielectric liquid, the dielectric composition of claim 1.

6. The electrical component as defined by claim 5, comprising a transformer, capacitor or cable.

* * * * *